United States Patent [19]
Betush

[11] Patent Number: 5,295,825
[45] Date of Patent: Mar. 22, 1994

[54] CONTROL SYSTEM FOR DENTAL HANDPIECES

[75] Inventor: Frank Betush, Carson, Calif.

[73] Assignee: Proma, Inc., Carson, Calif.

[21] Appl. No.: 996,686

[22] Filed: Dec. 24, 1992

[51] Int. Cl.$^5$ .......................... A61C 1/02; F16K 7/04
[52] U.S. Cl. ............................................. 433/28; 251/5
[58] Field of Search ................ 433/28, 98, 101, 79; 251/4, 5, 9

[56] References Cited

U.S. PATENT DOCUMENTS

| | | | |
|---|---|---|---|
| 2,483,954 | 10/1949 | Weiss | 251/5 X |
| 2,734,526 | 2/1956 | Aagaard | 251/5 X |
| 3,468,342 | 9/1969 | Craft | 251/5 X |
| 3,638,310 | 2/1972 | Austin, Jr. | 433/98 X |
| 3,755,899 | 9/1973 | Betush | 433/28 |
| 4,117,861 | 10/1978 | Betush | 433/98 X |
| 4,375,963 | 3/1983 | Betush | 433/28 |
| 4,610,630 | 9/1986 | Betush | 433/79 |
| 5,026,020 | 6/1991 | Betush | 251/5 |
| 5,097,868 | 3/1992 | Betush | 251/9 X |
| 5,158,453 | 10/1992 | Brockway | 433/28 |

FOREIGN PATENT DOCUMENTS 2147394  5/1985  United Kingdom ................ 433/98

*Primary Examiner*—John G. Weiss
*Assistant Examiner*—Nicholas D. Lucchesi

[57] ABSTRACT

A control system for a dental handpiece, and the like, for supplying a pressurized drive fluid, pressurized air, and water to the handpiece, and which includes a holder for the handpiece having an internal pinch valve which is operated whenever the handpiece is inserted or removed from the holder. A control module is provided which actually controls the flow of the various fluids to the handpiece. The control module includes a pinch lever which engages the various tubes carrying the fluids to the handpiece, and it also includes a swell tube which responds to pressurized fluid from the handpiece holder whenever the handpiece is removed. A linkage system couples the swell tube to the pinching lever in the control module. A feature of the control system is that a pressurized fluid of relatively low pressure is controlled by the insertion and removal of the handpiece from the holder, and it acts as a pilot to cause the control module to exert sufficient force on the various tubes carrying the fluids to the handpiece so as to achieve a positive control over the flow of the fluids.

14 Claims, 5 Drawing Sheets

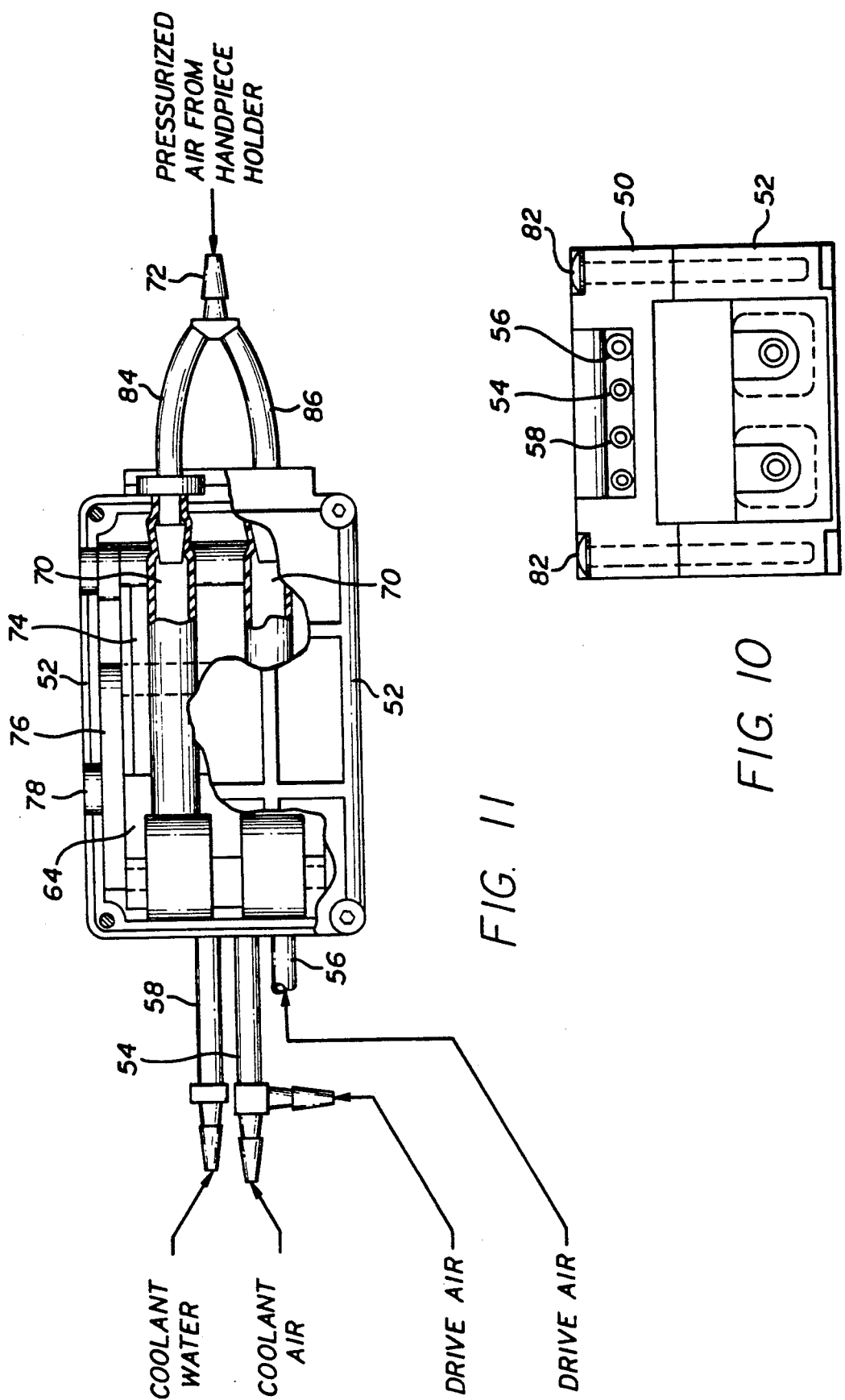

CONTROL SYSTEM FOR DENTAL HANDPIECES

BACKGROUND OF THE INVENTION

As stated in U.S. Pat. No. 4,117,861, which issued Oct. 3, 1978 to the present inventor, it is the usual practice in present-day dental offices to use a number of separate handpieces which are driven at high speeds by compressed air. In many instances, the high speed air driven handpieces also emit a spray of water and air as a coolant.

It is the common practice in the prior art for such handpieces to be supported on individual brackets which, in turn, are mounted on a console adjacent to the dental chair. Compressed air and pressurized water are supplied to the various handpieces in the prior art equipment through individual tubes. The air and water are obtained from the usual mains, and the flow thereof to the console is usually controlled by foot-operated valves.

In the prior art, additional valves are provided at the console so that the flow of the pressurized air and water to the individual handpieces may also be controlled. With such prior art equipment, the dentist causes the air and water to be supplied to the console by actuating his foot-operated valves; and he then causes the air or water, or both, to be supplied to a selected handpiece, by actuating appropriate valves in the console.

The valves in the prior art consoles, in addition to being complex and expensive, are difficult to operate, and they often require both hands of the dentist to control them. The control unit of the present invention, on the other hand, provides an improved pinch valve control system for distributing the pressurized air and water to the various dental handpieces associated with the console, and by which each handpiece is automatically activated, as it is selected by the dentist.

It will also become evident as the present description proceeds that although the pinch valve control system of the present invention is described in conjunction with dental handpieces, it has wider application in the art wherever the flow of fluid through a supply tube is to be controlled.

U.S. Pat. No. 3,755,899 which issued Sep. 4, 1973 to the present inventor describes apparatus in which dental handpieces are supported in individual holders on pivotally mounted arms, and each arm includes a pinch block at one end which pinches a corresponding flexible tube to prevent the flow of fluid to the handpiece when the holder is in its down position; but which permits the flow of fluid through the tube to the selected handpiece when the holder is in its up position. Therefore, in using the apparatus described in the patent, the dentist selects a particular handpiece from its holder, and he then flips the holder to its up position so as to activate the handpiece.

U.S. Pat. No. 4,117,861 discloses a pinch valve dental handpiece console which has certain advantages over the holder described in U.S. Pat. No. 3,755,899 referred to above in that it is less expensive to construct, and in that it operates by the insertion and withdrawal of the handpiece to and from its holder and there is no need for the dentist to flip the holder to its up position.

The control system of the present invention involves a pinch valve dental handpiece console which is similar in some respects to the console described in U.S. Pat. No. 4,117,861. The control system of the invention also includes pinch valve control modules which are respectively coupled to the handpiece holders and which operate in conjunction with the holders to control the operation of each dental handpiece selected by the dentist. In the control system of the present invention one such holder and one such control module are used to hold and control the operation of each dental handpiece.

The primary objective of the control system of the present invention is to:

a. select and activate a particular handpiece simply by the dentist removing it from its corresponding holder, and to deactivate the handpiece by the dentist returning it to its holder;

b. direct the flow of pressurized operating fluids to the selected handpiece; and c. coordinate and direct to the selected handpiece the coolant water, coolant air and atomization of the coolant water with the coolant air.

In a typical dental office a number of holders/control module sets incorporated in the control system of the present invention are mounted on a usual console stand which may be attached to the dental chair. The console may have the same general configuration, for example, as the console disclosed in U.S. Pat. No. 4,610,630 which issued on Sep. 9, 1986 to the present inventor. The number of holders/control module sets which can be supported on the console stand of the control system of the present invention is theoretically limited only by the supply pressure and flow required for each handpiece.

The control module of the invention is usually, but not exclusively, used to control the flow paths of water and air to a selected handpiece. The control module, per se, has general utility which is not limited to the control system to be described in the following specification. For example, the control module may be used in conjunction with the pinch toggle valve of U.S. Pat. No. 5,097,868 which issued to the present inventor on Mar. 24, 1992, as a water control to flush the dental cuspidor and fill the patient's cup.

In addition, the control module may be used as a water supply pressure-actuated anti-syphon shut-off valve. Such a valve is used to protect the city water supply from contamination due to "suck-back" from the dental treatment unit during periods of negative city water supply pressure. In this application the control module causes the valve to open and supply the dental treatment unit with city water only when adequate water pressure exists, and it serves to shut off the water flow path if the pressure drops below a selected threshold.

SUMMARY OF THE INVENTION

The invention provides an improved control system for one or more dental handpieces which is similar and more economical than previous systems and easier to operate. The control system of the invention includes a unique pinch valve holder unit for each dental handpiece and a unique pinch valve control module which is coupled to each holder unit and which assists in the control of each selected handpiece. As described above, the pinch valve control module has general application.

Figure 2:
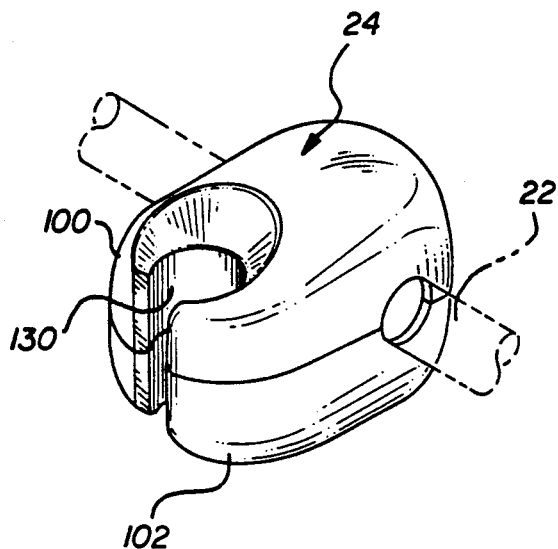
Figure 3:
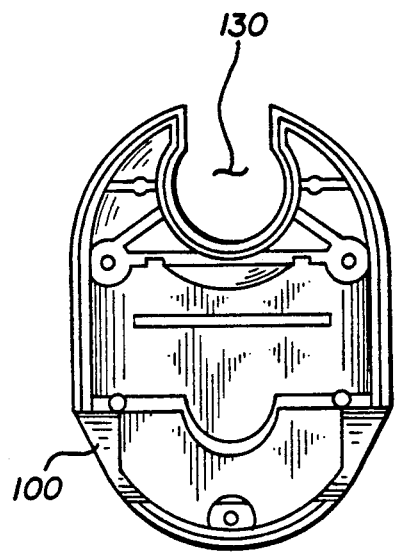
Figure 4:
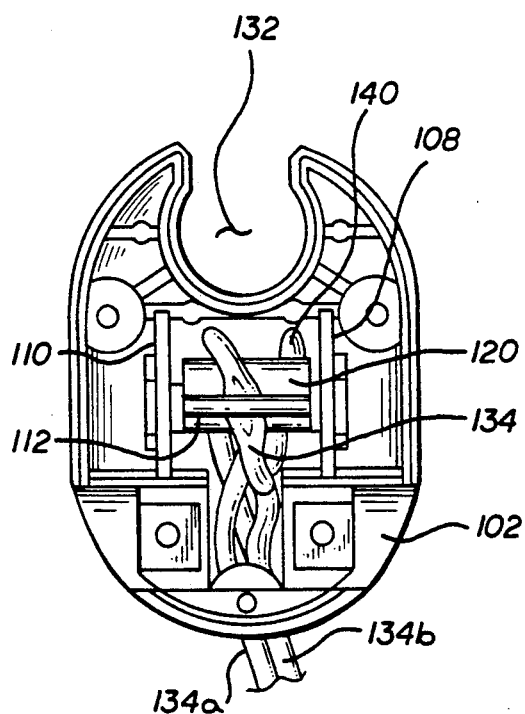
Figure 5:
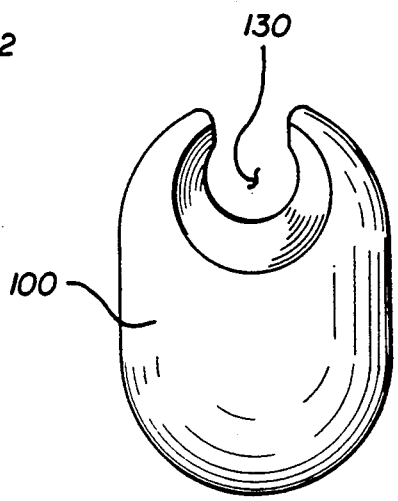
Figure 6:
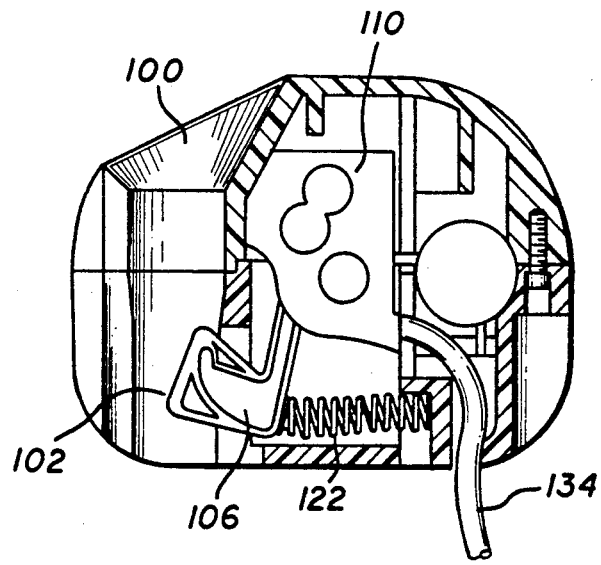
Figure 7:
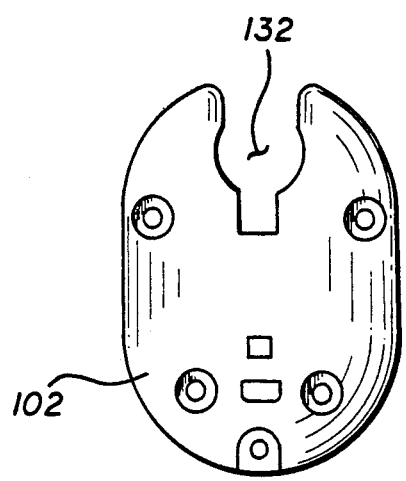
Figure 8:
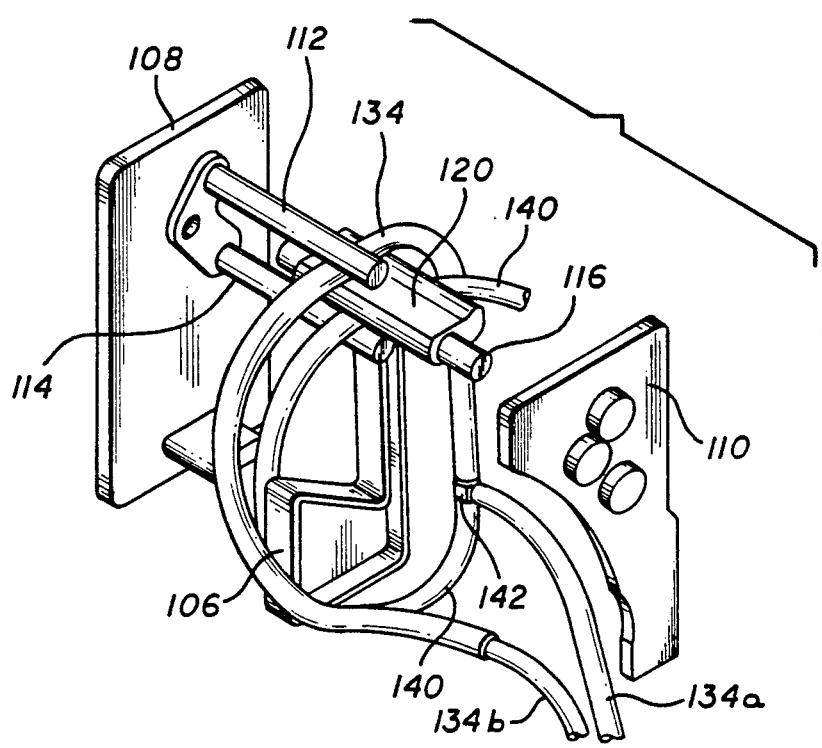
Figure 9:
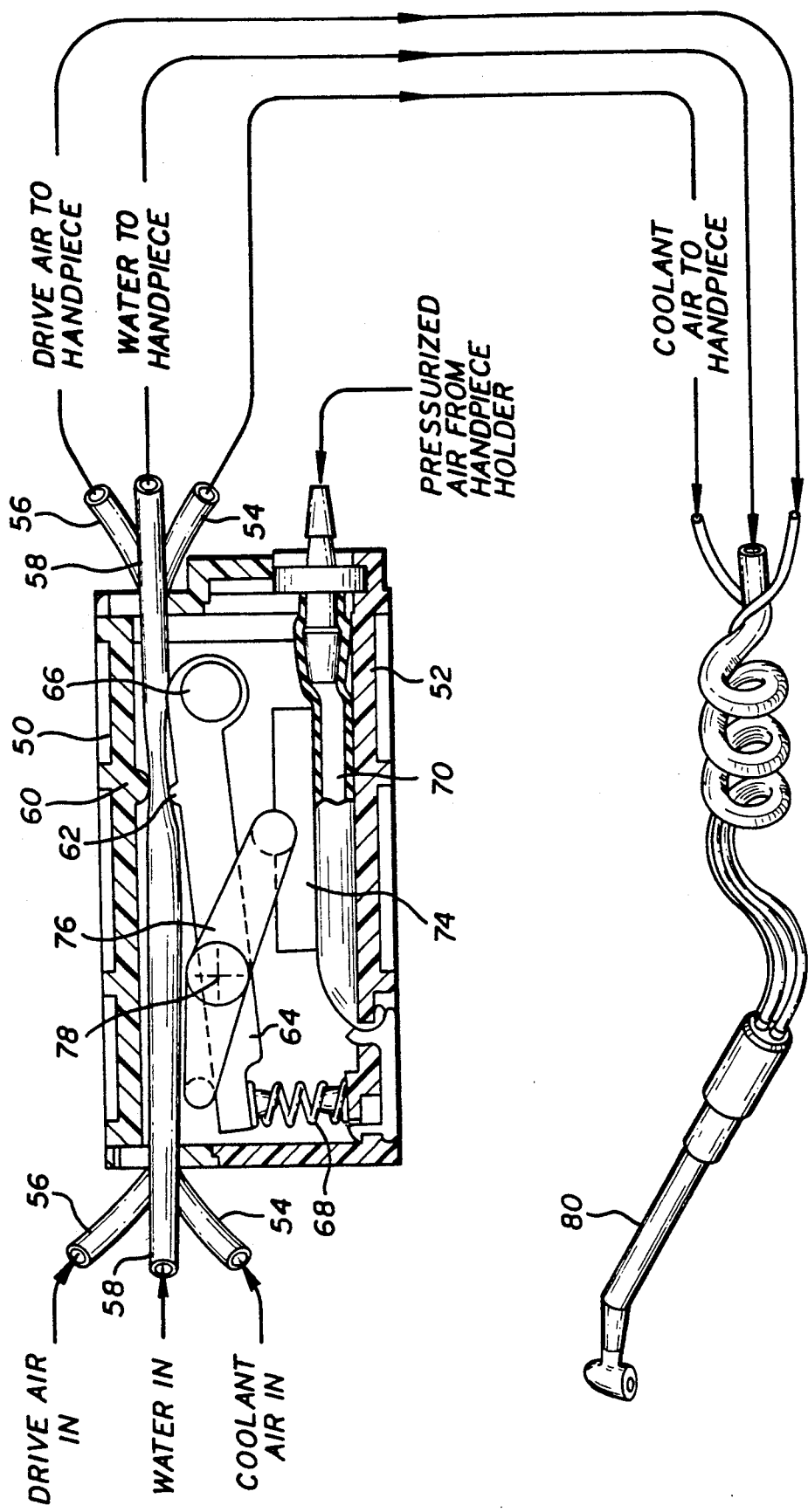

FIG. 2 is a perspective view of a pinch valve dental handpiece holder constructed in accordance with the concepts of the present invention;

FIG. 3 is a rear view of the upper half of the holder of FIG. 2;

FIG. 4 is a rear view of the lower half of the holder of FIG. 2;

FIG. 5 is an external view of the upper half of the holder of FIG. 2;

FIG. 6 is a side view, partly in section, of the holder of FIG. 2;

FIG. 7 is an external view of the lower half of the holder of FIG. 2;

FIG. 8 is a perspective representation of the actuator assembly which is included in the holder of FIG. 2;

FIG. 9 is a side sectional view of the pinch valve control module;

FIG. 10 is an end view of the control module taken from the right in FIG. 9; and FIG. 11 is a bottom view of the control module, partly broken away and partly in section.

DETAILED DESCRIPTION OF THE ILLUSTRATED EMBODIMENT

Figure 1:
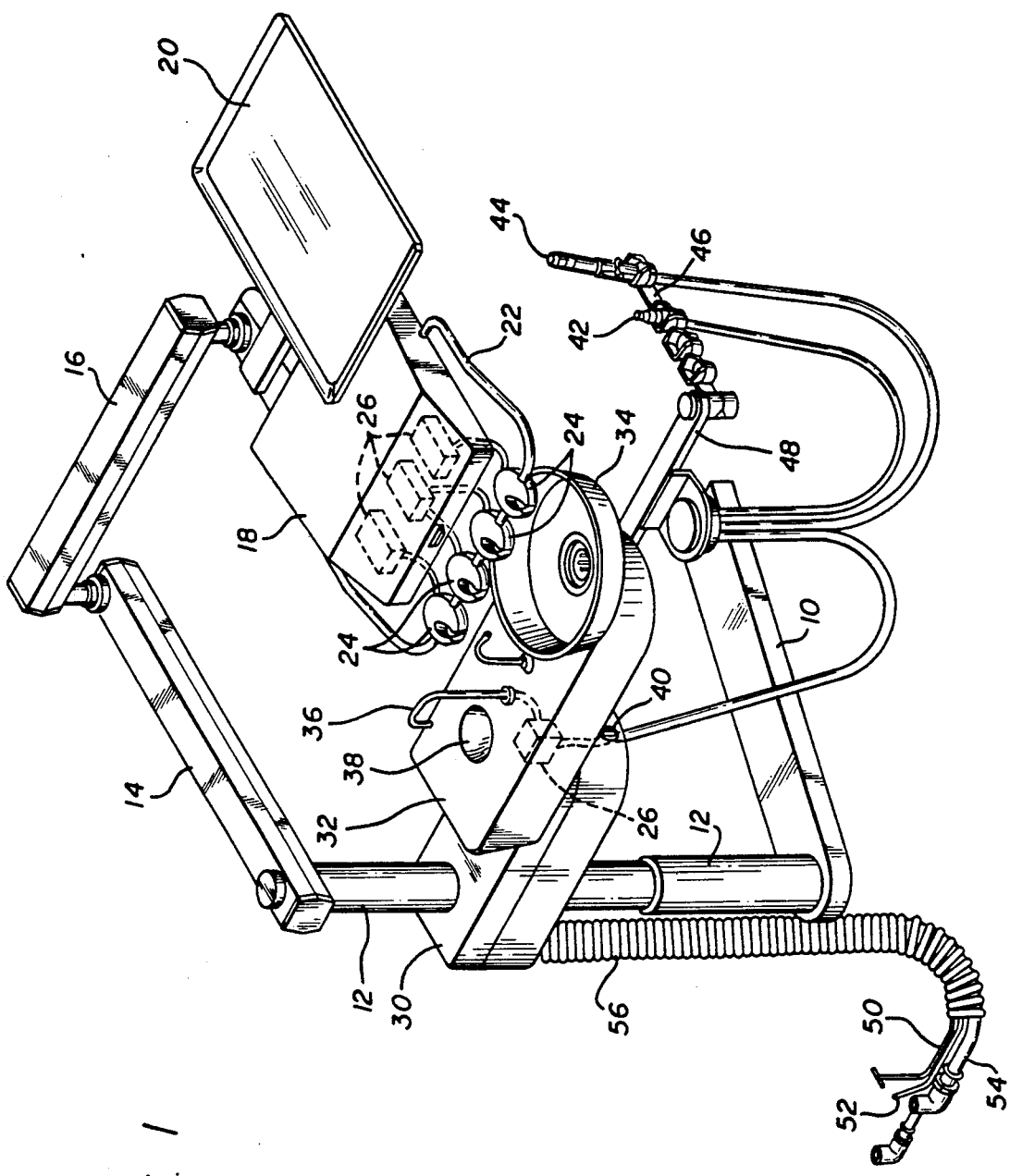
FIG. 1 is a perspective representation of a dental console stand for supporting various dental instruments, and which also serves to support the handpiece holder/- control module sets of the control system of the present invention.

The dental instrument stand shown in FIG. 1 is similar in some respects to the stand illustrated and described in U.S. Pat. No. 4,610,630 as mentioned above. The stand of FIG. 1 includes, for example, an arm 10 which may be attached to the side of the upper structure of a dental chair. A post 12 extends upwardly from arm 10, and a further arm 14 is pivotally mounted to the upper end of post 12. Another arm 16 is pivotally mounted to the distal end of arm 14, and a control unit 18 is pivotally mounted to the distal end of arm 16. A usual dental tray 20 is attached to the control unit 18, as shown.

The control unit 18 includes a bar 22 which is looped around the front of the control unit, and a plurality handpiece holders 24 are mounted on the bar which extends through the individual holders. The holders are rotatable to any desired angular position, and movable along the bar to any desired linear position. The holders are held in position on bar 22 by appropriate set screws (not shown). The handpiece holders 24 represent one of the units of the control system of the present invention, as will be described. A number of control modules 26 are mounted in the control unit 18, and the control modules are coupled to corresponding ones of the handpiece holders 24. The control modules represent a second component of the control system of the invention, as will be described.

A platform 30 is mounted on the post 12, and extends radially outwardly from the post. A further platform 32 is mounted on platform 30, and a usual dental cuspidor 34 is supported on platform 32. A drinking water tube 36 is also mounted on platform 34 for dispensing water into an appropriate patient's cup held in cavity 38. Water is supplied to the tube 36 by means of a toggle pinch valve 40 which may be of the type illustrated and described in U.S. Pat. No. 5,097,868, referred to above. The toggle pinch valve is coupled through a further control module 26 to the tube 36 so that water may be supplied through the tube.

A number of additional dental instruments, such as the instruments 42 and 44, are removably supported on a further arm 46 which, in turn, is pivotally coupled to an arm 48 extending under platform 32.

Pressurized air and water is supplied to the handpieces supported on the handpiece holders 24 through a number of conduits and tubes 52 and 54 which are contained in a flexible cable 56, and which extend into the interior of post 12, and through the arms 14 and 16 to the control modules 26 mounted in the control unit 18.

One of the handpiece holders 24 is shown in FIGS. 2–8. The handpiece holder 24 has a plastic casing which includes an upper half 100 and a lower half 102. The inside configuration of the upper half 100 is shown in FIG. 3, and the inside configuration of the lower half 102 is shown in FIG. 4. The external face of the upper half 100 is shown in FIG. 5, and the outer face of the lower half 102 is shown in FIG. 7. FIG. 6, as mentioned above, is a side view, partly in section, of the casing including the upper half 100 and lower half 102.

As best shown in FIGS. 6 and 8, an actuator 106 is pivotally mounted between two support brackets 108 and 110. A plurality of dowel pins 112, 114 and 116 extend between the support brackets 108 and 110. The actuator 106 is attached to a bracket 120 which, in turn, is rotatably mounted on dowel pin 116. A compression spring 122 biases the actuator in a clockwise direction in the view of FIG. 6. The upper half 100 of the handpiece casing includes a slot 130 (FIGS. 2, 3 and 5), and the lower half 102 of the Oasing includes a slot 132 (FIGS. 4 and 7). A handpiece is received in the slots 130 and 132, and is supported between the upper half 100 and lower half 102 of the handpiece holder. When the handpiece is in place, it forces actuator 106 against compression spring 122 to turn the bracket 120 about dowel pin 116 to a first position, and when the handpiece is removed, spring 122 causes actuator 106 to turn the bracket 120 about the dowel pin 116 to a second angular position.

A tube 134 is looped around the bracket 120 to extend between the bracket and the dowel pin 112. The tube 134 enters the housing of the handpiece holder through a first end 134a and its exits the housing through a second end 134b. When the handpiece is removed from the holder, spring 122 biases the actuator 106 to turn the bracket 120 about the dowel 116 to a position in which it squeezes the tube 134 against the dowel pin 112 to cut off the flow of fluid through tube 134. When the handpiece is inserted into the holder, actuator 106 turns bracket 120 about dowel pin 116 against the force of spring 122 to a second angular position in which the pinching action on tube 134 is removed, so that fluid may flow through the tube.

An exhaust tube 140 is coupled to the end 134a of tube 134 through an appropriate fitting 142. The exhaust tube extends between the dowel pin 114 and bracket 120 so that the exhaust tube is opened when the handpiece is inserted into the handpiece holder, but is pinched closed when the handpiece is removed. Tube 140 provides an exhaust for the fluid in the end 134a of tube 134 when the handpiece is placed in the holder. As shown in FIGS. 9, 10 and 11, each pinch valve control module 26 is contained in a housing having a top 50 and a bottom 52. Three tubes 54, 56 and 58 extend through the top portion of the housing adjacent to one another from one end of the housing to the other. The three tubes extend across a protuberance 60 extending down from the top side of the top 50 of the housing and a protuberance 62 which is mounted on a pinching lever 64, the pinching lever being pivoted on a pivot pin 66.

The pinching lever 64 is biased by a compression spring 68 to cause the protuberance 62 to pinch the tubes 54, 56 and 58 in conjunction with the protuberance 60.

A pair of swelling tubes, such as swelling tube 70, are mounted in the bottom half 52 of the housing, and pressurized air from the handpiece holder is introduced to the swelling tube through a fitting 72. A slide actuator 74 is mounted on the swelling tube 70, and one end of a lever 76 is supported on the slide actuator. Lever 76 is pivoted about a pin 78 at its midpoint, and the other end of lever 76 engages the pinching lever 64.

When pressurized air is introduced to the swelling tubes 70 from the handpiece holder, the swelling tube causes the slide actuator 74 to move upwardly and the end of lever 76 to slide along the slide actuator and pivot about the pivot point 78. This causes the other end of the slide actuator to move the pinching lever 64 against the compression of spring 68 to cause the protuberant 62 to move away from the protuberant 60 so that the three tubes 54, 56 and 58 are opened. As shown in FIG. 9, the tube 56 applies drive air to the handpiece 80, the tube 54 supplies coolant air to the handpiece, and the tube 58 supplies coolant water to the handpiece.

As described above, each handpiece 80 (FIG. 9) is held in a separate holder 24 (FIG. 2), and each holder has a separate control module 26 such as the control module of FIGS. 9-11 associated with it. In operating the system, the dentist, by operation of an appropriate foot control, (not shown) releases coolant air, drive air and coolant water to all of the control modules 26 of FIG. 1, and these fluids are carried by the tubes 54, 56 and 58 in each of the control modules. However, until one of the dental handpieces is selected, the fluids are cut off in each of the control modules by the pinching action of protuberances 60 and 62.

However, if a handpiece is selected from one of the holders, the holder then causes pressurized air to flow to the corresponding control module 26 through its fitting 72 which, as described above, causes the swelling tubes 70 to swell and actuate the corresponding pinching lever 64 through the action of lever 76, so that the tubes 54, 56 and 58 in the particular control module are unblocked and the various fluids are supplied to the selected handpiece 80.

As shown in FIG. 10, the top portion 50 and bottom portion 52 of the control module 26 are held together by screws, such as the screws 82. As best shown in FIG. 11, the fitting 72 which receives pressurized air from the handpiece holder is coupled to the two swelling tubes 70 which are mounted side by side on the bottom 52 of the housing by tubes 84 and 86. Accordingly, pressurized fluids flow through the control module 26 through the tubes 54, 56 and 58 when the swelling tubes 70 are inflated. The swelling tubes are inflated whenever a dental handpiece, such as handpiece 80, is removed from its holder 24. Then, when the handpiece is replaced in its holder, the corresponding exhaust line 140 (FIG. 8) is opened, permitting the swelling tubes 70 to deflate, and for the control module 26 again to pinch the tubes 54, 56 and 58, so as to stop the flow of fluids through the control module.

The invention provides, therefore, an improved control system for dental handpieces which relies on a separate control module for each handpiece. The removal of a handpiece from its holder opens a pilot valve in the holder which introduces pressurized fluid to the controller, so that the controller may perform the necessary functions to open the tubes supplying fluids to the handpiece.

While a particular embodiment of the invention has been shown and described, modifications may be made. It is intended in the claims to cover all modifications which come within the true spirit and scope of the invention.

I claim:

1. A control system for a dental handpiece including a control module, a tube coupled to said control module for supplying pressurized fluid to said control module, a handpiece holder including pinch valve means for receiving said tube so as to cause the flow of the pressurized fluid to the control module to occur only when the handpiece is removed from the holder, at least one tube for supplying a selected fluid to the handpiece, and said control module including pinch valve means engaging said last named tube for causing the selected fluid to be supplied to said handpiece only in response to the pressurized fluid from the handpiece holder.

2. The control system defined in claim 1, in which said handpiece holder includes a pivotally mounted actuator moveable between a first angular position and a second angular position when the handpiece is inserted into the holder, and spring means coupled to said actuator for returning the actuator to its first angular position when the handpiece is removed from the holder, and a bracket coupled to the actuator and engaging said tube, said bracket being movable by said actuator to pinch the tube only when the handpiece is in the holder.

3. The control system defined in claim 2, and which includes an exhaust tube connected to said first named tube and extending through said holder in a position to be engaged by said bracket and to be pinched thereby only when said actuator is in its second angular position when the handpiece is removed from the holder.

4. The control system defined in claim 1, in which said control module includes a pivotally mounted pinching lever engaging said tube supplying the selected fluid to the handpiece, at least one swell tube coupled to the tube from the handpiece holder, linkage means coupling the swell tube to the pinching lever for moving the pinching lever from a first angular position to a second angular position so as to cause the pinching lever to pinch the tube supplying the selected fluid to the handpiece in response to the pressurized fluid from the handpiece holder.

5. The control system defined in claim 4, and which includes spring means engaging said pinching lever for returning said pinching lever to its first angular position in the absence of pressurized fluid from said holder.

6. The control system defined in claim 5, in which said linkage means includes a second lever coupled to said pinching lever, and a slide actuator coupling said swell tube to said second lever.

7. The control system defined in claim 1 and which includes a plurality of tubes for supplying a corresponding plurality of fluids to said handpiece, and said pinch-valve of said control module engages all of said tubes of said last-named plurality for causing all of the fluids to be supplied to the handpiece in response to the pressurized fluid from the handpiece holder.

8. A control system for dental handpieces, and the like, which includes a stand, and a control unit mounted on the stand; a plurality of control modules mounted in said control unit, a rod attached to said control unit, a corresponding plurality of handpiece holders mounted on said rod and angularly and linearly adjustable with respect to said rod, a corresponding plurality of handpieces supported in respective ones of said holders, a first plurality of tubes coupled to respective ones of said control modules for supplying pressurized fluid to said control modules, each of said handpiece holders including pinch-valve means receiving a corresponding one of said tubes of said first plurality to cause the flow of the pressurized fluid to the corresponding control module to occur only when the corresponding handpiece is removed from its holder, a second plurality of tubes for supplying a selected fluid to respective ones of said handpieces, and each of said control modules including pinch-valve means engaging corresponding ones of said tubes of said second plurality for causing the selected fluid to be supplied to the handpieces in response to the pressurized fluid from the respective holders corresponding thereto.

9. The control system defined in claim 8, in which each of said handpiece holders includes a pivotally mounted actuator moveable between a first angular position and a second angular position when the corresponding handpiece is inserted into the holder, and spring means coupled to said actuator for returning the actuator to its first angular position when the handpiece is removed from the holder, and a bracket coupled to said actuator and engaging said one of said tubes and movable by said actuator to pinch the last named tube only when the handpiece is in the holder.

10. The control system defined in claim 9, and which includes a plurality of exhaust tubes connected to respective ones of said tubes of said second plurality and each of said exhaust tubes extending through a corresponding one of said holders in position to be engaged by said bracket so as to be pinched only when said actuator is in its second angular position when the corresponding handpiece is removed from the holder corresponding thereof.

11. The control system defined in claim 8, in which each of said control modules includes a pivotally mounted pinching lever engaging a corresponding tube of said second plurality, at least one swell tube coupled to a corresponding tube of said first plurality and extending from the corresponding handpiece holder; linkage means coupling the swell tube to the pinching lever for mounting the pinching lever from a first angular position to a second angular position so as to cause the pinching lever to pinch the corresponding tube of said second plurality in response to pressurized fluid from the corresponding handpiece holder.

12. The control system defined in claim 11, and which includes spring means engaging said pinching lever for returning the pinching lever to its first angular position in the absence of pressurized fluid from the corresponding handpiece holder.

13. The control system defined in claim 11, in which said linkage means includes a second lever coupled to said pinching lever, and a slide actuator coupling said swell tube to said second lever.

14. The control system defined in claim 8, and which includes a plurality of tubes extending through each of said control modules for supplying a corresponding plurality of fluid to each of said handpieces, and in which said pinch- valve of each of said control modules engages all of said tubes of said last-named plurality so as to cause all of the fluids to be supplied to a corresponding handpiece in response to the pressurized fluid from a corresponding handpiece holder.

* * * * *